United States Patent
Min et al.

(10) Patent No.: US 11,730,441 B2
(45) Date of Patent: Aug. 22, 2023

(54) METHODS AND DEVICES FOR DETECTING HEART SOUNDS TO MONITOR CARDIAC FUNCTION

(71) Applicant: PACESETTER, INC., Sylmar, CA (US)

(72) Inventors: Xiaoyi Min, Simi Valley, CA (US); Kyungmoo Ryu, Palmdale, CA (US); Stephanie C. Sun, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1084 days.

(21) Appl. No.: 16/057,650

(22) Filed: Aug. 7, 2018

(65) Prior Publication Data

US 2020/0046312 A1 Feb. 13, 2020

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/0205* (2013.01); *A61B 5/686* (2013.01); *A61B 5/725* (2013.01);
(Continued)

(58) Field of Classification Search
CPC ........... A61B 5/00; A61B 5/0205; A61B 7/02; A61B 7/04; A61B 5/0031; A61B 5/686;
(Continued)

(56) References Cited

U.S. PATENT DOCUMENTS

2008/0013747 A1* 1/2008 Tran .................... A61B 7/04
381/67
2008/0119749 A1 5/2008 Haro et al.
(Continued)

OTHER PUBLICATIONS

Nigam, Vivek, and Roland Priemer. "A dynamic method to estimate the time split between the A2 and P2 components of the S2 heart sound." Physiological measurement 27.7 (2006): 553. (Year: 2006).*
(Continued)

*Primary Examiner* — Christian Jang
*Assistant Examiner* — Mitchell E Alter
(74) *Attorney, Agent, or Firm* — The Small Patent Law Group LLC; Dean D. Small

(57) ABSTRACT

Methods and implantable medical devices (IMDs) are provided for monitoring a cardiac function of a heart. A heart sound sensor is configured to sense heart sound signals of the subject. The IMD includes a memory to store program instructions. The IMD includes a processor that, when executing the program instructions, is configured to identify S2 signal segment from the heart sound signals, analyze the S2 signal segment to identify a pulmonary valve signal (P2 signal) and an aortic valve signal (A2 signal) within an S2 signal segment of the heart sound signals. The processor is configured to determine a time interval between the A2 and P2 signals, characterize the S2 signal segment to exhibit a first type of S2 split based on the time interval, and identify a cardiac condition based on a comparison of the first type of S2 split and a cardiac condition matrix.

18 Claims, 8 Drawing Sheets

| | Right Heart | Left Heart | Great Vessels | Septum |
|---|---|---|---|---|
| Normal Split | | | | |
| Wide Split | RBBB | Pre-Excitation of LV, LV Pacing, Premature LV Beats | Pulmonary Stenosis, Pulmonary Arterial Hypertension | |
| Split During Expiration | RV Pacing | Hypertrophic Cardiomyopathy LBBB | Aortic Stenosis | |
| Split During both Inspiration and Expiration: Fixed Split | Right Heart Failure | | Pulmonary Hypertension | Atrial Septal Defect |
| Split during both Inspiration and Expiration | | LBBB Pre-Excitation Of RV, RC Pacing, Premature RV Beats | Aortic Stenosis | |
| Single S2: Either from Loss of A2 or Loss of P2 | | | Severe Aortic Stenosis, Severe Aortic Regurgitation, Congenital Absence of Pulmonary Valve | |

(51) Int. Cl.
| | |
|---|---|
| *A61N 1/365* | (2006.01) |
| *A61B 7/02* | (2006.01) |
| *A61B 5/0205* | (2006.01) |
| *A61N 1/02* | (2006.01) |
| *A61B 5/08* | (2006.01) |
| *A61B 5/113* | (2006.01) |
| *A61N 1/39* | (2006.01) |
| *A61N 1/372* | (2006.01) |

(52) U.S. Cl.
CPC ............ *A61B 5/7282* (2013.01); *A61B 7/023* (2013.01); *A61N 1/36514* (2013.01); *A61N 1/36585* (2013.01); *A61B 5/0809* (2013.01); *A61B 5/0816* (2013.01); *A61B 5/113* (2013.01); *A61B 2562/0219* (2013.01); *A61B 2562/0247* (2013.01); *A61N 1/025* (2013.01); *A61N 1/37211* (2013.01); *A61N 1/39622* (2017.08)

(58) Field of Classification Search
CPC ....... A61B 5/725; A61B 5/7282; A61B 7/023; A61B 2562/0219; A61B 2562/0247; A61B 5/0809; A61B 5/0816; A61B 5/113; A61N 1/365; A61N 1/36514; A61N 1/36585; A61N 1/37211; A61N 1/39622; A61N 1/025
See application file for complete search history.

(56) References Cited

U.S. PATENT DOCUMENTS

| | | | |
|---|---|---|---|
| 2012/0046564 | A1* | 2/2012 | Koh ..................... A61B 5/686 600/515 |
| 2012/0101393 | A1* | 4/2012 | Zhang ................. A61B 5/0452 600/484 |
| 2013/0053913 | A1* | 2/2013 | Koh ........................ A61B 7/04 607/17 |
| 2016/0058318 | A1* | 3/2016 | Borjigin ............... A61B 5/7275 600/516 |
| 2020/0077892 | A1* | 3/2020 | Tran ..................... A61B 5/6806 |

OTHER PUBLICATIONS

Mgdob, H. M., et al. "Application of Morlet transform wavelet in the detection of paradoxical splitting of the second heart sound." Computers in Cardiology, 2003. IEEE, 2003. (Year: 2003).*

Yildirim, Isa, and Rashid Ansari. "A robust method to estimate time split in second heart sound using instantaneous frequency analysis." 2007 29th Annual International Conference of the IEEE Engineering in Medicine and Biology Society. IEEE, 2007 (Year: 2007).*

Tang et al. "Discrimination of Aortic and Pulmonary Components from the Second Heart Sound Using Respiratory Modulation and Measurement of Respiratory Split" Applied Sciences MDPI; 2017 (16 pages).

* cited by examiner

| | Right Heart | Left Heart | Great Vessels | Septum |
|---|---|---|---|---|
| 710 — Normal Split | | | | |
| 712 — Wide Split | RBBB | Pre-Excitation of LV, LV Pacing, Premature LV Beats | Pulmonary Stenosis, Pulmonary Arterial Hypertension | |
| 714 — Split During Expiration | RV Pacing | Hypertrophic Cardiomyopathy LBBB | Aortic Stenosis | |
| 716 — Split During both Inspiration and Expiration: Fixed Split | Right Heart Failure | LBBB Pre-Excitation Of RV, RC Pacing, Premature RV Beats | Pulmonary Hypertension | Atrial Septal Defect |
| 718 — Split during both Inspiration and Expiration | | | Aortic Stenosis | |
| 720 — Single S2: Either from Loss of A2 or Loss of P2 | | | Severe Aortic Stenosis, Severe Aortic Regurgitation, Congenital Absence of Pulmonary Valve | |

Figure 7

METHODS AND DEVICES FOR DETECTING HEART SOUNDS TO MONITOR CARDIAC FUNCTION

BACKGROUND

Embodiments of the present disclosure generally relate to methods and implantable medical devices (IMDs) for detecting a cardiac function of a heart.

It has been proposed to utilize heart sounds in connection with monitoring certain cardiac functions. Heart sounds are the noises generated by the beating heart and the resultant flow of blood, and are typically referred to as S1, S2, S3 and S4. An S1 heart sound is caused by the sudden block of reverse blood flow due to closure of the atrioventricular valves (mitral and tricuspid) at the beginning of ventricular contraction. When the ventricles begin to contract, so do the papillary muscles in each ventricle. The papillary muscles are attached to the tricuspid and mitral valves via chorda tendinae, which bring the cusps of the valve closed (chorda tendinae also prevent the valves from blowing into the atria as ventricular pressure rises due to contraction). The closing of the inlet valves prevents regurgitation of blood from the ventricles back into the atria. The S1 sound results from reverberation within the blood associated with the sudden block of flow reversal by the valves.

An S2 heart sound is caused by the sudden block of reversing blood flow due to closure of the aortic valve and pulmonary valve at the end of ventricular systole, i.e beginning of ventricular diastole. As the left ventricle empties, the left ventricular pressure falls below the pressure in the aorta and aortic blood flow quickly reverses back toward the left ventricle, catching the aortic valve leaflets and is stopped by aortic (outlet) valve closure. Similarly, as the pressure in the right ventricle falls below the pressure in the pulmonary artery, the pulmonary (outlet) valve closes. The S2 sound results from reverberation within the blood associated with the sudden block of flow reversal.

However, opportunity remains for methods and devices to utilize heart sounds to monitor cardiac functions.

SUMMARY

In accordance with embodiments herein, an implantable medical device (IMD) is provided. The IMD includes a heart sound sensor configured to sense heart sound signals of the subject. The IMD includes a memory to store program instructions. The IMD includes a processor that, when executing the program instructions, is configured to identify and S2 signal segment from the heart sound signals, analyze the S2 signal segment to identify a pulmonary valve signal (P2 signal) and an aortic valve signal (A2 signal) within the S2 signal segment of the heart sound signals. The processor is configured to determine a time interval between the A2 and P2 signals, characterize the S2 signal segment to exhibit a first type of S2 split based on the time interval between the A2 and P2 signals, and identify a cardiac condition based on a comparison of the first type of S2 split and a cardiac condition matrix.

Optionally, the processor is configured to characterize the first type of S2 split to be one of a normal split, a wide split, a fixed split, or a paradoxical split. Additionally or alternatively, the processor is configured to identify the cardiac condition based on the cardiac condition matrix that is divided based on multiple types of S2 split and multiple local heart regions. The cardiac condition matrix further includes different cardiac conditions associated with each combination of the S2 split type and local heart region. Optionally, the local heart regions include a right heart region, a left heart region, a greater vessel region and a septum. The processor is configured to identify, for the first type of the S2 split corresponding right heart-related conditions, left heart-related conditions, and greater vessel-related conditions.

Optionally, the IMD includes a respiration sensor configured to sense a respiration signal of the subject. The processor is configured to apply a bandpass filter to the respiration signal to identify the P2 signal and the A2 signal from the S2 signal segment. Additionally or alternatively, the respiration sensor comprises at least one of an accelerometer, a pressure sensor, and an impedance sensor that are configured to indicate a respiratory phase of the subject.

The respiration signal includes an expiration phase and an inspiration phase that form at least part of a respiratory cycle of the subject. The processor is configured to identify expiration and inspiration time intervals between the P2 signal and the A2 signal in connection with the expiration and inspiration phases. Additionally or alternatively, the processor is configured to extract the P2 signal and the A2 signal based on a peak of the A2 signal and the slope of the P2 signal. Optionally, the IMD includes an electromyography (EMG) sensor configured to detect a cardiac signal of the subject. The processors configured to use the cardiac signal to apply a bandpass filter to the heart sound signal to identify the P2 signal and the A2 signal.

Optionally, the processor is configured to record the cardiac condition over time for the subject to develop a patient tracking record indicating at least one of a new cardiac conditions or changes in existing cardiac conditions. Additionally or alternatively, the processor is configured to monitor the time interval between the A2 and P2 signals over time and record changes in the time interval in connection with monitoring for heart failure. Optionally, the IMD includes a pulse generator to deliver pacing therapy based in part on programmed AV and VV delays. The processor is configured to monitor the time interval between the A2 and P2 signals over time and record changes in the time interval in connection with adjustments and at least one of the programmed AV or VV delay is for the IMD.

In accordance with embodiments herein, a method to manage an implantable medical device (IMD) is provided. The method includes receiving heart sound signals of the subject. The method includes identifying and S2 signal segment from the heart sound signals, analyzing the S2 signal segment to identify a pulmonary valve signal (P2 signal) and an aortic valve signal (A2 signal) within the S2 signal segment of the heart sound signals. The method includes characterizing the S2 signal segment to exhibit a first type of S2 split based on the time interval between the A2 and P2 signals, and identifying a cardiac condition based on a comparison of the first type of S2 split and a cardiac condition matrix.

Optionally, the method may include characterizing the first type of S2 split to be one of a normal split, a wide split, a fixed split, or paradoxical split. Additionally or alternatively, the identifying operation includes comparing the first type of S2 split to the cardiac condition matrix that is divided into multiple types of S2 split and multiple local heart regions. The cardiac condition matrix further including different cardiac conditions associated with each combination of the S2 split type and local heart region. Additionally or alternatively, the local heart regions include a right heart region, a left heart region, and a greater vessel region. Optionally, the method includes identifying the first type of S2 split, corresponding to right heart-related conditions, left heart rate-related conditions, and greater vessel-related conditions.

Optionally, the method includes receiving a respiration signal of the subject and applying a bandpass filter to the respiration signal to identify the P2 signal and the A2 signal from the S2 signal segment. Additionally or alternatively, the respiration sensor comprises at least one of an accelerometer, a pressure sensor, an impedance sensor that are configured to indicate a respiratory phase of the subject. Additionally or alternatively, the method includes extracting the P2 signal and the A2 signal based on the peak of the A2 signal and a slope of the P2 signal relative to the respiratory phase.

Optionally, the method includes receiving a respiration signal of the subject. The respiration signal including an expiration phase and an inspiration phase that form a respiratory cycle of the subject. Additionally or alternatively, the method includes identifying the P2 signal and the A2 signal based on expiration and inspiration phases. Optionally, the method includes receiving a cardiac signal of the subject, and applying a bandpass filter to the heart sound signal to identify the P2 signal and the A2 signal. Additionally or alternatively, the method includes recording the cardiac condition over time for the subject to develop a patient tracking record indicating at least one of a new cardiac conditions or changes in existing cardiac conditions. Additionally or alternatively, the method includes monitoring the time interval between the A2 and P2 signals over time and record changes in the time interval in connection with monitoring heart failure.

BRIEF DESCRIPTION OF THE DRAWINGS

FIG. 7 illustrates a cardiac condition matrix, in accordance with an embodiment.

DETAILED DESCRIPTION

Figure 1:
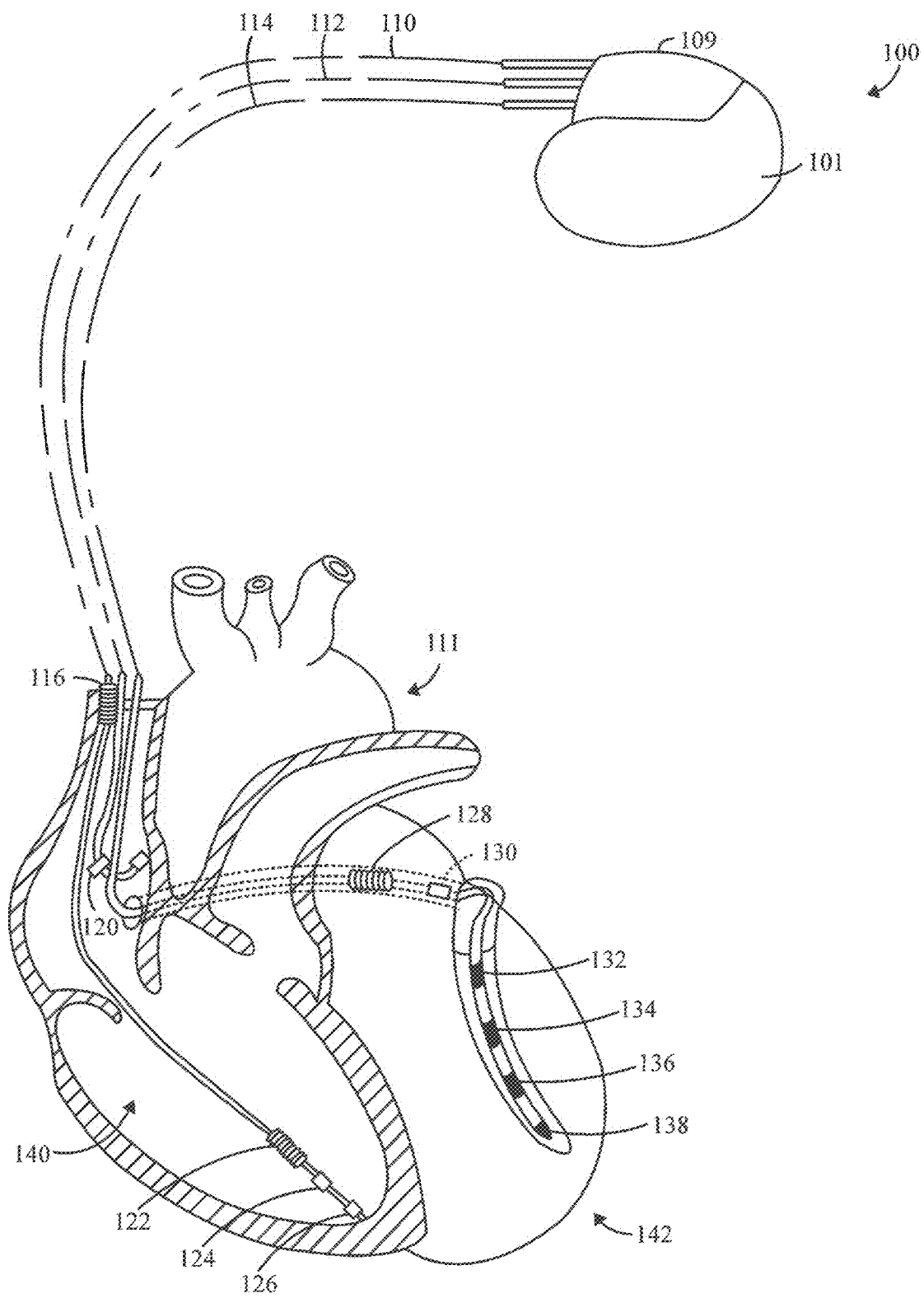
FIG. 1 illustrates an implantable medical device (IMD), in accordance with an embodiment.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example and simply illustrates certain example embodiments.

The systems and methods described herein may employ structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and/or the like. The IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

In accordance with an embodiment, methods and devices are provided that extract, from an S2 signal segment, a pulmonary valve component (P2 component of S2) and an aortic valve component (A2 component of S2). Responsive to inspiration, the chest wall expands and causes the intrathoracic pressure to become negative. An inspiration phase further induces an increase in venous blood return from the body into the right atrium via the superior and inferior venae cava. Additionally, during inspiration, a reduction is experienced in blood volume returning from the lungs into the left atrium, and an increase is experienced in blood volume in the right ventricle. The pulmonary valve stays open longer during ventricular systole due to an increase in ventricular emptying time. Alternatively, the aortic valve closes slightly earlier due to a reduction in left ventricular volume and ventricular emptying time. The P2 component of S2 is delayed relative to that of the A2 component of S2. The delay is represented as a slight broadening or even "split" of the second heart sound.

Responsive to an expiration phase, the chest wall collapses and decreases the negative intrathoracic pressure. There is an increase in blood return to the right ventricle versus the left ventricle, and the right ventricle volume pressure is reduced. The pulmonary valve closes earlier such that an overlap of the closing of the aortic valve, and the split may not be heard. The pressure in the right ventricle tries to open the pulmonary valve, during inspiration. The pressure in the pulmonary artery tries to close the pulmonary valve, during expiration. The closure of the pulmonary valve may be delayed due to the pressure in the right ventricle increased during inspiration, opposing the pressure in the pulmonary artery and keeping it open longer than in expiration.

Conventional methods do not provide feedback regarding a timing relationship between a pulmonary valve (P2 signal) and an aortic valve (A2 signal) of an S2 signal segment.

Embodiments herein utilize the timing relationship between P2 and A2 to obtain information regarding the cardiac condition of the subject (e.g., the patient). In accordance with embodiments herein, a processor identifies the S2 signal segment from the heart sound signals. Optionally, the processor may identify the S2 signal segment based on the heart sound signals alone or in combination with the cardiac signal and/or respiratory signals. The processor analyzes the S2 signal segment to identify the P2 signal and the A2 signal within the S2 signal segment from the heart sound signals. The processor determines a time interval between the A2 and P2 signals. The time interval represents a temporal difference between the A2 and P2 signals for a particular point in a respiratory cycle. The time interval may vary between inspiration and expiration phases and is referred to as inspiration time interval and expiration time interval. The processor characterizes the S2 signal segment to exhibit a first type of S2 split based on the time intervals between the A2 and P2 signals during different respiration cycles. The processor identifies a cardiac condition based on a comparison of the first type of the S2 split and a cardiac condition matrix. The cardiac condition matrix includes a collection of cardiac conditions associated with select combinations of local heart regions, activation of the local heart regions and WS2 split types. For example, the local heart region may have right ventricle (RV) pacing or left ventricle (LV) pacing of cardiac conditions. Additionally or alternatively, the cardiac condition matrix includes historical cardiac conditions associated with great vessels and septum. For example, the processors may compare an individual patient history and/or a patient database to determine if the great vessels and/or the septum includes cardiac conditions.

FIG. 1 illustrates an implantable medical device (IMD) 100 in electrical communication with multiple leads implanted into a patient's heart 111. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 includes a housing 101 to hold the electronic/computing components. The housing 101 (which is often referred to as the "can", "case", "encasing", or "case electrode") may be programmably selected to act as the return electrode for certain stimulus modes. The housing 101 further includes a connector 109 with a plurality of terminals 102, 105, 106, 107, 108 (shown in FIG. 2).

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132, an LV electrode 134, an LV electrode 136, and an LV electrode 138. The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber).

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like. In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

When selecting a target venous branch for the LV lead 114, several factors may be taken into account. For example, it may be desirable to maximize the LV mass that may be captured by the LV lead 114. Accordingly, to maximize LV mass exposure, certain venous branches may be preferred for positioning the LV lead 114. Further, a diameter and trajectory of the venous branch are also considered to ensure that the venous branch will support the chronic stability of the LV lead 114. Passive fixation of the LV lead 114 may be established through the anatomy of the host venous branch which causes the LV lead 114 to extend the distal portion thereof in a manner that differs from the LV lead's preformed shape. Optionally, additional factors to be considered when placing the LV lead 114 may include reducing myocardial capture thresholds, avoiding atrial and phrenic nerve stimulation and the like. After the LV lead 114 is positioned, the LV pacing vectors may be selected.

The LV electrode 138 (also referred to as P4) is shown as being the most "distal" LV electrode with reference to how far the electrode is from the right ventricle 140. The LV electrode 132 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2. M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and the RV coil 122 or another electrode remote from the left ventricle 142). Below is a list of exemplary bipolar sensing vectors with LV cathodes that may be used for sensing using the LV electrodes D1, M2, M3, and P4 and the RV coil 122. It may be noted, that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode.

Implantable Medical Device

Figure 2:
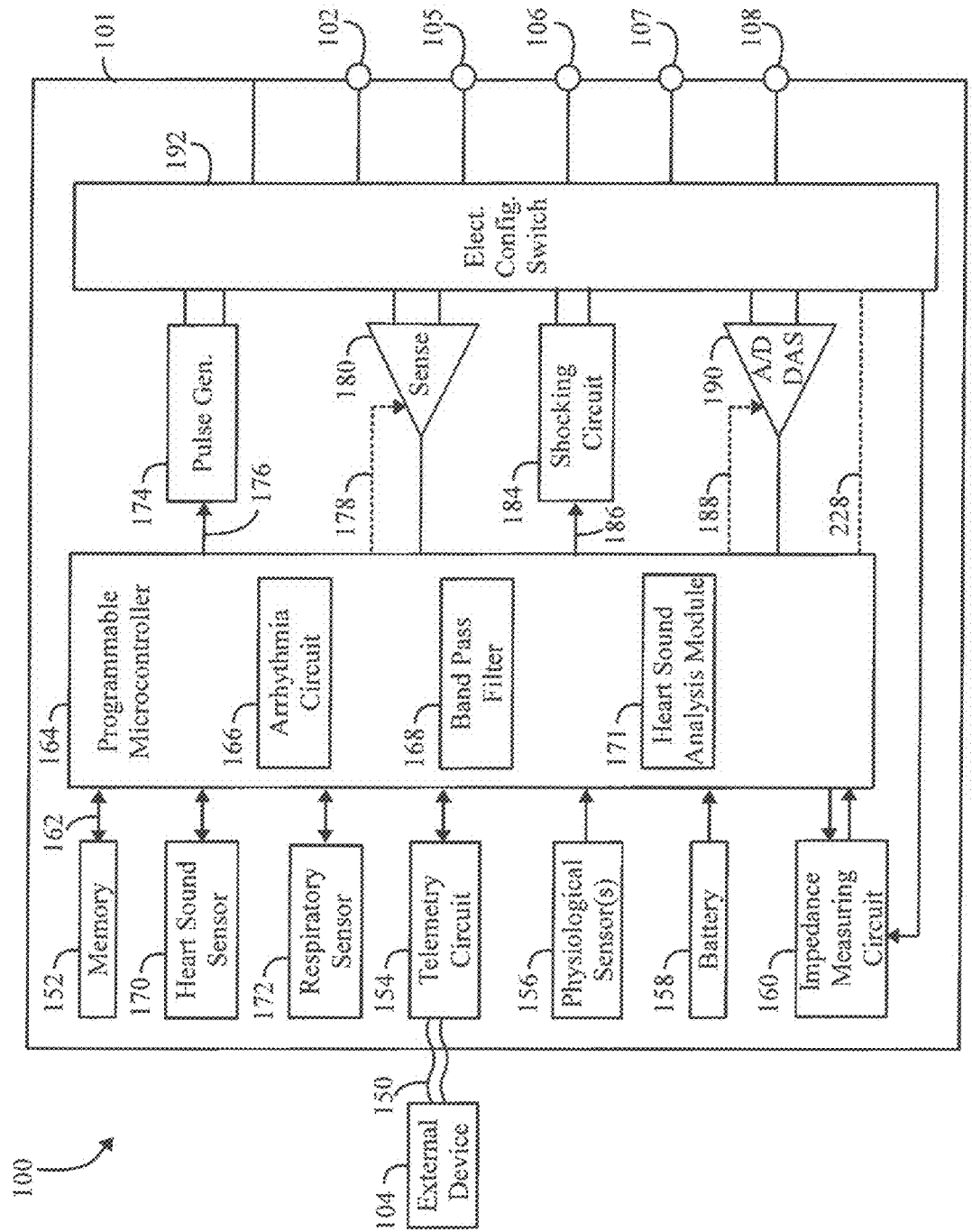
FIG. 2 illustrates a schematic view of the IMD, in accordance with an embodiment.

FIG. 2 illustrates a schematic view of the IMD 100. The IMD 100 has a housing 101 to hold the electronic/computing components. The housing 101 (which is often referred to as the "can," "case," "encasing," or new to me makes "case electrode") may be programmably selected to act as the return electrode for certain stimulus modes. The housing 101 further includes a connector (not shown) with a plurality of terminals 102, 105, 106, 107 and 108. The terminals may be connected to electrodes that are located in various locations within and about the heart. For example, the terminals may include: an electrode 102 to be coupled to a first electrode (e.g., a tip electrode) located in a first chamber; an electrode 105 to be coupled to a second electrode (e.g., tip electrode) located in a second chamber; an electrode 106 to be coupled to an electrode (e.g., ring) located in the first chamber; an electrode 107 to be coupled to an electrode located (e.g., ring electrode) in the second chamber; and an electrode 108 to be coupled to an electrode (e.g., coil) located in the SVC 116. The type and location of each electrode may vary. For example, the electrodes may include various combinations of a ring, a tip, a coil and shocking electrodes and the like.

The IMD 100 includes a programmable microcontroller 164 that controls various operations of the IMD 100, including cardiac monitoring and stimulation therapy. The microcontroller 164 includes a microprocessor (or equivalent control circuitry), one or more processors, RAM and/or ROM memory, logic and timing circuitry, state machine circuitry, and I/O circuitry. The IMD 100 further includes an atrial and/or ventricular pulse generator 174 that generates stimulation pulses for connecting the desired electrodes to the appropriate I/O circuits, thereby facilitating electrode programmability. The switch 192 is controlled by a control signal 186 from the microcontroller 164.

A single pulse generator 174 is illustrated. Optionally, the IMD 100 may include multiple pulse generators, similar to the pulse generator 174, where each pulse generator is coupled to one or more electrodes and controlled by the microcontroller 164 to deliver select stimulus pulse(s) to the corresponding one or more electrodes. The IMD 100 includes sensing circuitry 180 selectively coupled to one or more electrodes that perform sensing operations, through the switch 192 to detect the presence of cardiac activity in any chamber of the heart 111. The output of the sensing circuitry 180 is connected to the microcontroller 164 which, in turn, triggers, or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits 180, similar to the sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or a bipolar sensing configuration.

The IMD 100 further includes an analog-to-digital (A/D) data acquisition system (DAS) 190 coupled to one or more electrodes via the switch 192 to sample cardiac signals across any pair of desired electrodes. The A/D converter 190 is configured to acquire intracardiac electrogram signals, convert the raw analog data into digital data and store the digital data for later processing and/or telemetric transmission to an external device 104 (e.g., a programmer, local transceiver, or a diagnostic system analyzer). The A/D converter 190 is controlled by a control signal 188 from the microcontroller 164.

The microcontroller 164 includes an arrhythmia circuit 166 for analyzing cardiac activity signals sensed by the sensing circuit 180 and/or the A/D converter 190. The arrhythmia circuit 166 is configured to analyze cardiac signals sensed by the electrode and to deliver a therapy based on the cardiac signals. The arrhythmia detection circuit 166 declaring arrhythmias, in response to which, the microcontroller 164 determines an appropriate therapy. For example, responsive to the arrhythmia detection circuit 166 identifying a tachyarrhythmia, the microcontroller 164 directs the shocking circuit 184 to deliver a shock and/or directs the ATP pulse generator 174 to deliver an ATP therapy. The microcontroller 164 controls the timing of the stimulation pulses, the timing of refractory periods, blanking intervals, noise detection windows, evoked response windows, alert intervals, marker channel timing, and/or the like.

The microcontroller 164 is operably coupled to a memory 152 by a suitable data/address bus 162. The programmable operating parameters used by the microcontroller 164 are stored in the memory 152 and used to customize the operation of the IMD 100 to suit the needs of a particular patient. The operating parameters of the IMD 100 may be non-invasively programmed into the memory 152 through a telemetry circuit 154 in telemetric communication via communication link 150 (e.g., MICS, Bluetooth low energy, and/or the like) with the external device 104. The telemetry circuit 154 allows intracardiac electrograms, A2-P2 time interval, S2 Split types, cardiac conditions and status information relating to the operation of the IMD 100 (as contained in the microcontroller 164 and/or memory 152) to be sent to the external device 104 through the established communication link 150. The memory 152 also stores a cardiac condition matrix, as described herein that is utilized in connection with identifying cardiac conditions. As explained hereafter, the cardiac condition is determined by comparing the cardiac condition matrix to a type of S2 split that is exhibited during one or more cardiac cycles. The cardiac condition matrix is divided into multiple types of the S2 split and multiple local heart regions. The cardiac condition matrix includes different cardiac conditions associated with each combination of the S2 split type and local heart region. The local heart regions include a right heart region, a left heart region, and a greater vessel region. The microcontroller 164 is configured to identify, for a given type of the S2 split, one or more corresponding right heart-related conditions, left heart-related conditions, and greater vessel-related conditions.

The IMD 100 can further include one or more physiological sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. While shown as being included within the unit 100, the physiological sensor(s) 156 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 158 provides operating power to all of the components in the IMD 100. The battery 158 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries.

The IMD 100 further includes an impedance measuring circuit 160, which can be used for many things, including sensing respiration phase. The impedance measuring circuit 160 is coupled to the switch 192 so that any desired electrode and/or terminal may be used to measure impedance in connection with monitoring respiration phase.

The microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD 100.

In accordance with embodiments herein, the microcontroller 164 is electrically coupled to a heart sound sensor 170. The heart sound sensor 170 is configured to sense heart sound signals of the subject. The heart sound signal can include any signal indicative of at least a portion of a lease one heart sound of the subject. A heart sound of the subject can include an audible or mechanical noise or vibration indicative of blood flow through the heart or valve closures of the heart. Optionally, the heart sound signals may include an electrical or optical signal. The heart sound signals may represent a measurement, feature, characteristic, computation, or interval of at least a portion of at least one heart sound. For example, the heart sound signals may include at least one of an amplitude of a heart sound, a magnitude of the heart sound, a total energy of the heart sound, and interval between one heart sound feature and another heart sound feature, at least one heart sound characteristic normalized by at least one other heart sound characteristic, and/or the like.

The microcontroller 164 is electrically coupled to a respiratory sensor 172. The respiratory sensor 172 is configured to sense a respiration signal of the subject. The respiration signal can include any signal indicative of at least a portion of a lease one respiration signal of the subject. The respiration signal of the subject can include an audible or mechanical noise or vibration indicative of blood flow through the heart or valve closures of the heart. Optionally, the respiration signal may include an electrical or optical signal.

The respiration signal is indicating of respiratory phases (e.g, an expiration phase, an inspiration phase). For example, the respiratory signal may include at least one of an amplitude of a respiration, a magnitude of the respiration, a total energy of the respiration, and/or interval between one respiration feature and another respiration feature, at least one respiration characteristic normalized by at least one other respiration characteristic, and/or the like. The respiratory sensor 172 measures the analog signal indicative of the respiratory signal.

Optionally, the respiratory sensor 172 may include at least one of an accelerometer, a pressure sensor, and/or an impedance sensor that is configured to indicate a respiratory phase of the subject. The respiratory sensor 172 may include a pressure sensor configured to sense differences in pressure of the lungs corresponding to the respiratory phase of the subject. For example, the pressure sensor identifies changes in a movement by the lungs (e.g., inspiration phase, expiration phase) representing the respiratory phases of the subject. Optionally, the pressure sensor may include at least one of inspiration, and expiration, a transition between inspiration and expiration, a transition between expiration and inspiration, and/or the like. The respiratory sensor 172 may include an impedance sensor configured to sense differences in pressure of the lungs corresponding to the respiratory phases of the subject. For example, the impedance sensor may include a transthoracic impedance sensor configured to measure the respiratory phases of the lungs.

The microcontroller 164 includes a heart sound analysis (HSA) module 171 that implements the methods described herein. Among other things, the HSA model 171 analyzes the heart sound signals to identify the S2 signal segment and to identify, within the S2 signal segment, the P2 signal and the A2 signal. The HSA module 171 may identify the A2 and P2 signals in various manners. For example, one technique for identifying the A2 and P2 signals from the S2 signal segment is described in Tang, Hong, et al., "Discrimination of Aortic and Pulmonary Components from the Second Heart Sound Using Respiratory Modulation and Measurement of Respiratory Split," Jul. 4, 2017, which is hereby incorporated by reference. The HSA module 171 further determines the expiration and inspiration time intervals between the A2 and P2 signals and characterizes the A2 signal segment to exhibit a select type of S2 split based on the expiration and inspiration time intervals. The HSA module 171 also identifies a cardiac condition based on a comparison of the select type of the S2 split and a cardiac condition matrix.

Figure 3:
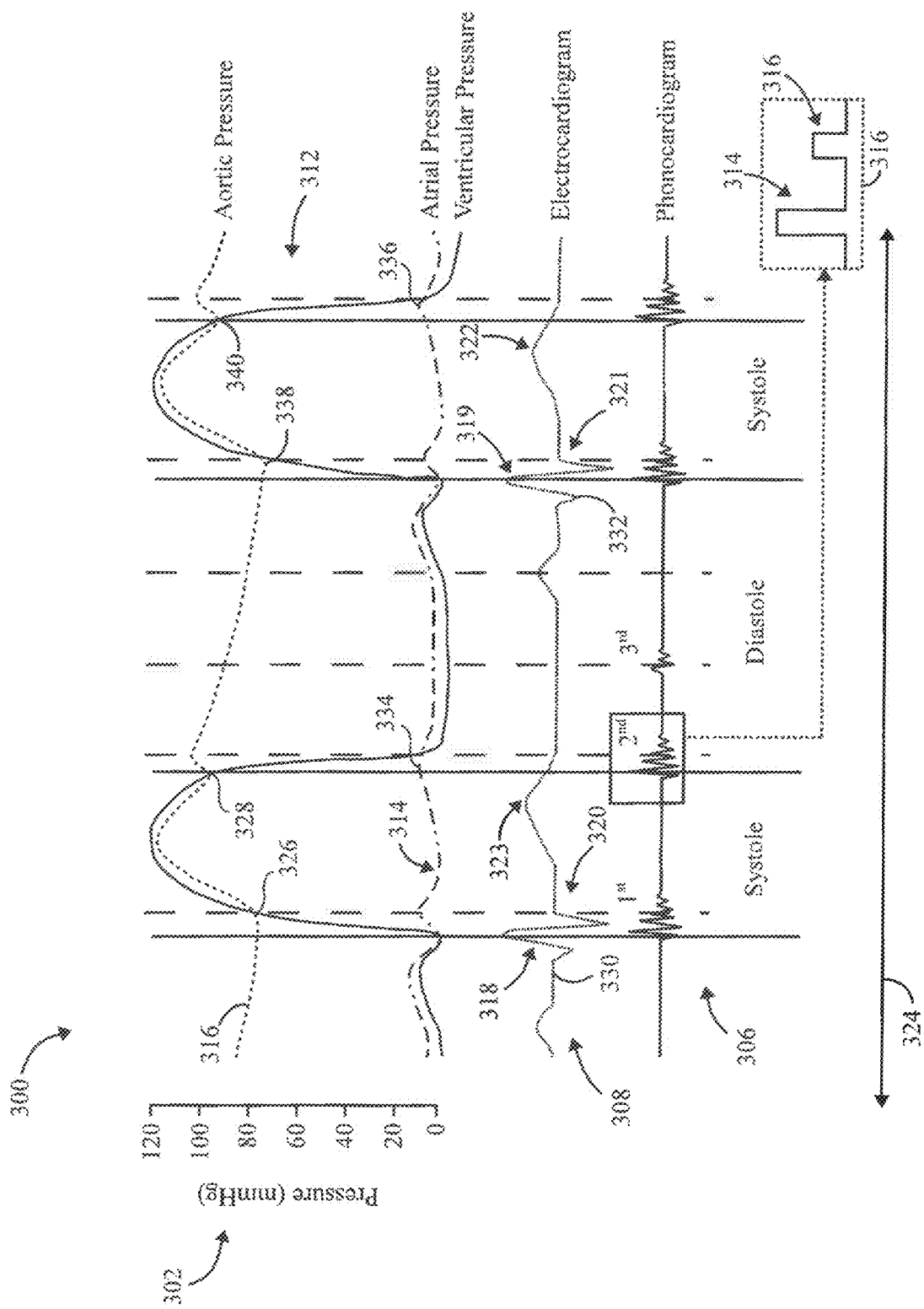
FIG. 3 illustrates a graphical representation of signals that are representative of various characteristics of the heart, in accordance with an embodiment.

FIG. 3 illustrates a graphical representation 300 of signals that are representative of various characteristics of the heart. A cardiac signal 308 is acquired at one or more electrodes and the sensing circuit 180 and/or the A/D DAS 190. For example, the cardiac signal 308 is shown over time for at least two cardiac cycles. A heart sound signal 306 is sensed by the heart sound sensor 170 and analyzed by the HSA module 171. FIG. 3 also illustrates aortic, atrial and ventricular pressures in connection with various cardiac events.

The heart sound signals 306 include an S2 signal segment. For example, the S2 signal segment is shown over time along the horizontal axis 324. The HSA module 171 is configured to identify the S2 signal segment of the heart sound signals 306. The HSA module 171 analyzes the S2 signal segment to identify a pulmonary valve signal (a P2 signal 316) and an aortic valve signal (an A2 signal 314) within the S2 signal segment of the heart sound signals 306. In FIG. 3, detail 326 is provided to illustrate the A2 and P2 signal components within the S2 signal segment. The A2 signal 314 and/or the P2 signal 316 are identified from the heart sound signals 306 by passing the frequencies between 5-200 Hz from the bandpass filter 168.

Optionally, the microcontroller 164 and/or HSA module 171 may use the cardiac signal 308 to identify timing markers that are used to align a search window to identify the A2 and P2 signals 314, 316. For example, the microcontroller 164 and/or HSA module 171 may identify the QRS complex 320-321 and one or more markers from the QRS complex 320-321 to determine an RR interval or more generally a cardiac cycle length. The microcontroller 164 and/or HSA module 171 may identify T waves 322, 323 separate from or based on the QRS markers. The microcontroller 164 and/or HSA module 171 overlay an A2 search window upon the S2 signal segment, where the heart sound signal segment within the A2 search window is analyzed to identify the A2 signal 314. The A2 search window may be positioned over the S2 signal segment at a point in time following a peak of the T wave by a predetermined time duration. For example, the predetermined time duration may be defined as a fixed value programmed by a clinician. Alternatively, the predetermined time duration may be automatically determined based on the length of the cardiac cycle (e.g., a percentage of the cycle length).

Once the A2 signal 314 is identified, a P2 search window is overlaid upon the S2 signal segment and the HSA module 171 analyzes the S2 signal segment to identify the P2 signal 316. Optionally, the A2 signal 314 and the P2 signal 316 may be identified in other manners.

Respiration Signal

Figure 4:
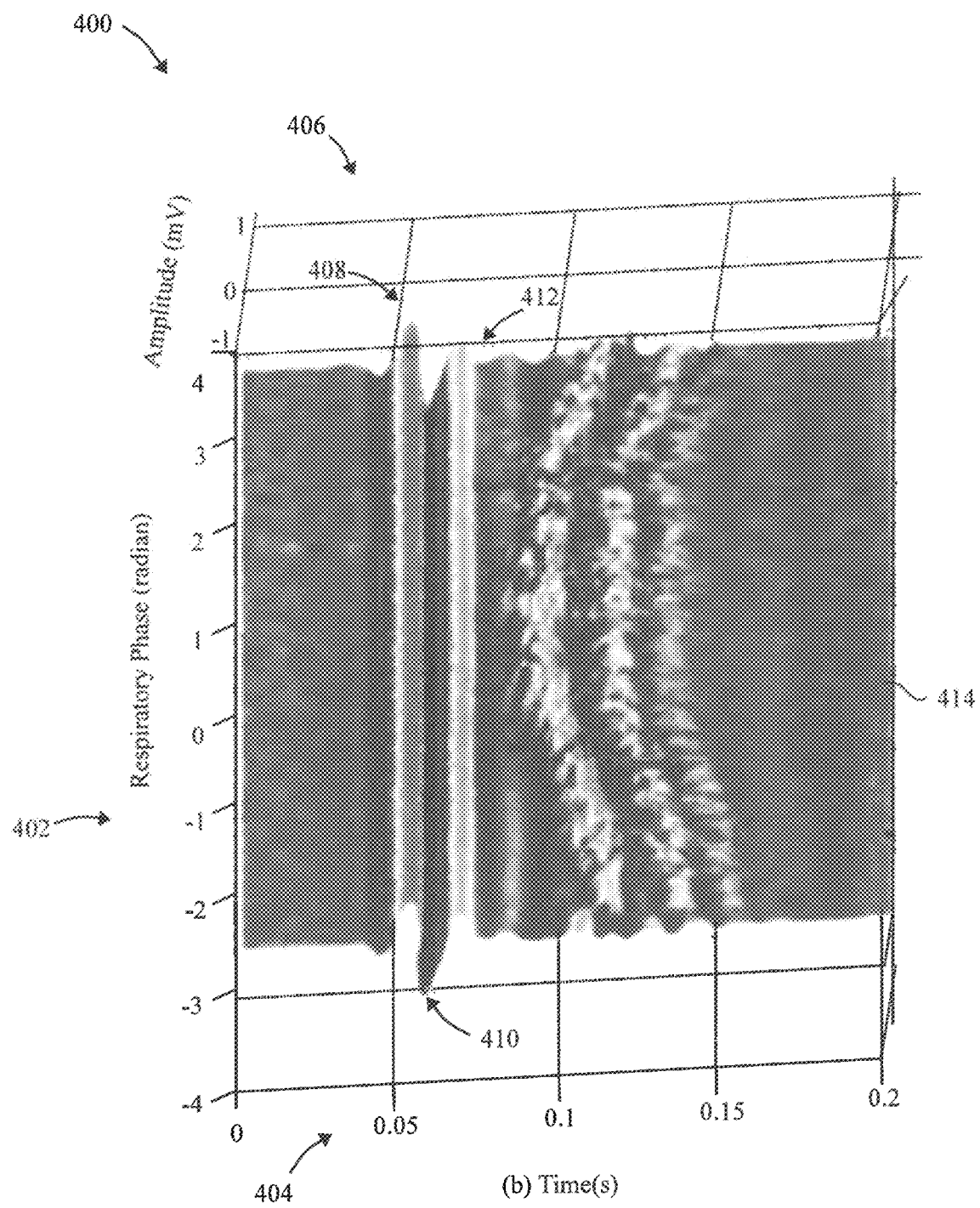
FIG. 4 illustrates a graphical representation of a respiration signal measured, in accordance with an embodiment.

FIG. 4 illustrates a graphical representation 400 of a respiration signal 414 measured in accordance with embodiments herein. The respiration signal 414 is shown along three different axes 402, 404, 406. A horizontal axis 404 represents time, a vertical axis 402 represents the respiratory phase, and a height axis 406 represents an amplitude of the respiration signal 414. The amplitudes are shown as millivolts that are identified by the respiratory sensor 172. For example, the height axis 406 includes three peaks 408, 410, 412 that represent the different respiratory phases of the respiration signal 414. The peaks 408 and 410 represent the expiration phase of the respiration signal 414. The peak 410 represents the inspiration phase of the respiration signal 414. For example, the inspiration phase and the expiration phase are example points along the respiratory phase of the respiration signal 414. The amplitudes of the peaks 408, 410, 412 are shown along the height axis 406.

Figure 5:
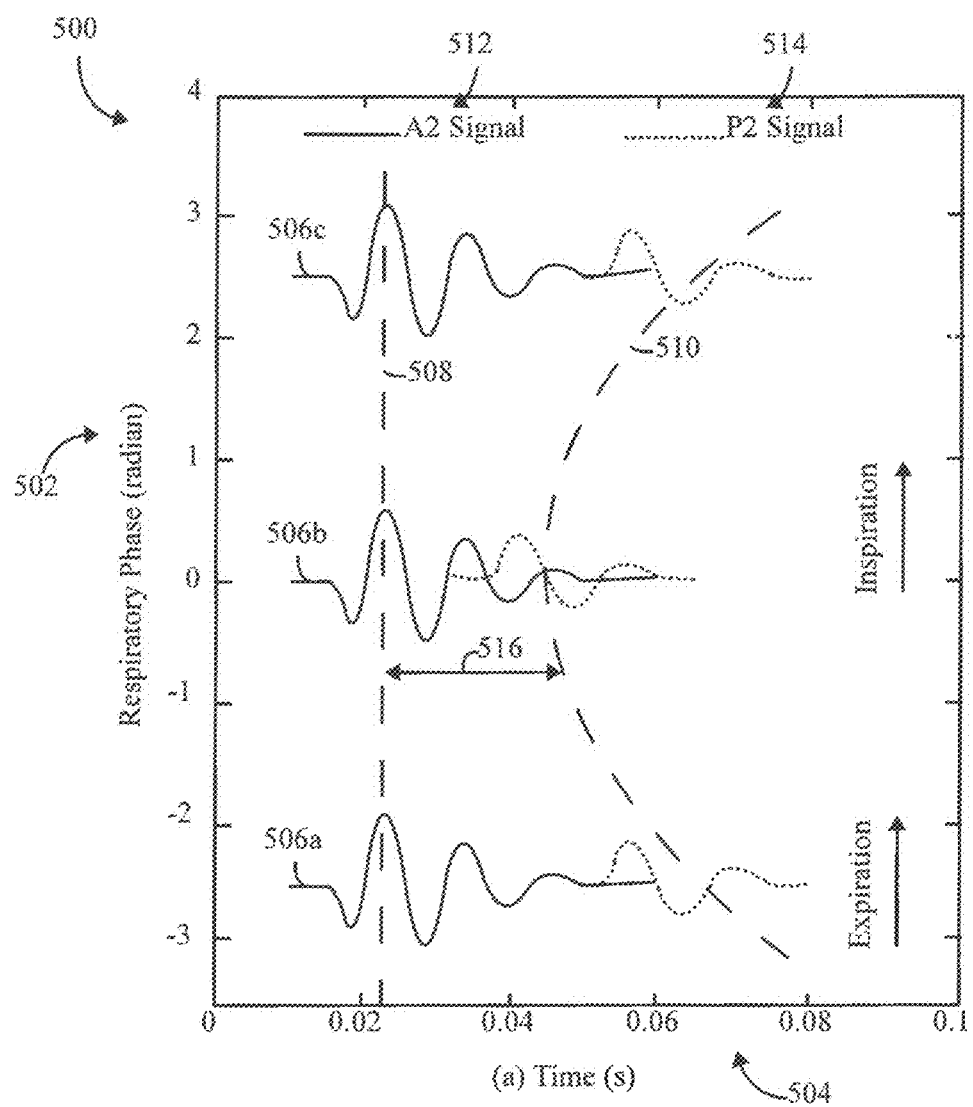
FIG. 5 illustrates a graphical representation of shifts in the A2 signal and P2 signal components relative to one another in connection with different respiratory phases at which the S2 signal segment occurs, in accordance with an embodiment.

FIG. 5 illustrates a graphical representation 500 of shifts in the A2 signal and P2 signal components relative to one another in connection with different respiratory phases at which the S2 signal segment occurs. FIG. 5 illustrates S2 signal segments 506A-C extends along a horizontal axis 504 representing time. For example, the S2 signal segments 506A-C corresponds to three points along the inspiration phase and the expiration phase. In accordance with embodiments herein, the microcontroller 164 collects first heart sound signals during an inspiration phase and second heart sound signals during an expiration phase. For example, from the first and second heart sound signals, the microcontroller 164 may determine the S2 signal segments 506A and 506C during an expiration phase and determine S2 signal segment 506B during an inspiration phase.

For example, the S2 signal segments 506A and 506C exhibit a first relation between the A2 signal 512 and P2 signal 514 in connection with the expiration phase (e.g, as monitored by the respiratory sensor 172). The S2 signal segments 506B exhibits a second relation between the A2 signal 512 and P2 signal 514 in connection with the inspiration phase. For example, the microcontroller 164 utilizes the respiration signals to determine which respiratory phase a particular combination of the A2 signal 512 and the P2 signal 514 are collected in connection with.

The P2 signal 514 may be identified based on morphology (e.g., amplitude and/or slope). For example, the microcontroller 164 analyzes a slope and/or derivative of the respiratory signals and/or S2 signal segment. The microcontroller 164 may compare the slope and/or the derivative relative to one or more the respiratory signals stored in the memory 152. The microcontroller 164 identifies the time interval 516 between the A2 and P2 signals 512, 514. For example, the microcontroller 164 calculates the time interval 516 between a characteristic of interest in the A2 and P2 signals 512, 514. The characteristic of interest may represent a maximum peak and/or slope in the A2 and P2 signals 512, 514.

The time intervals 516, determined in connection with a combination of S2 signal segments for inspiration and expiration phases of a respiratory cycle are utilized to characterize a type of the S2 split. For example, the S2 split may exhibit various types. Once the type is characterized for the S2 split, the microcontroller 164 identifies a cardiac condition based on a comparison of the type of the S2 split and a cardiac condition matrix.

S2 Split Types

Figure 6:
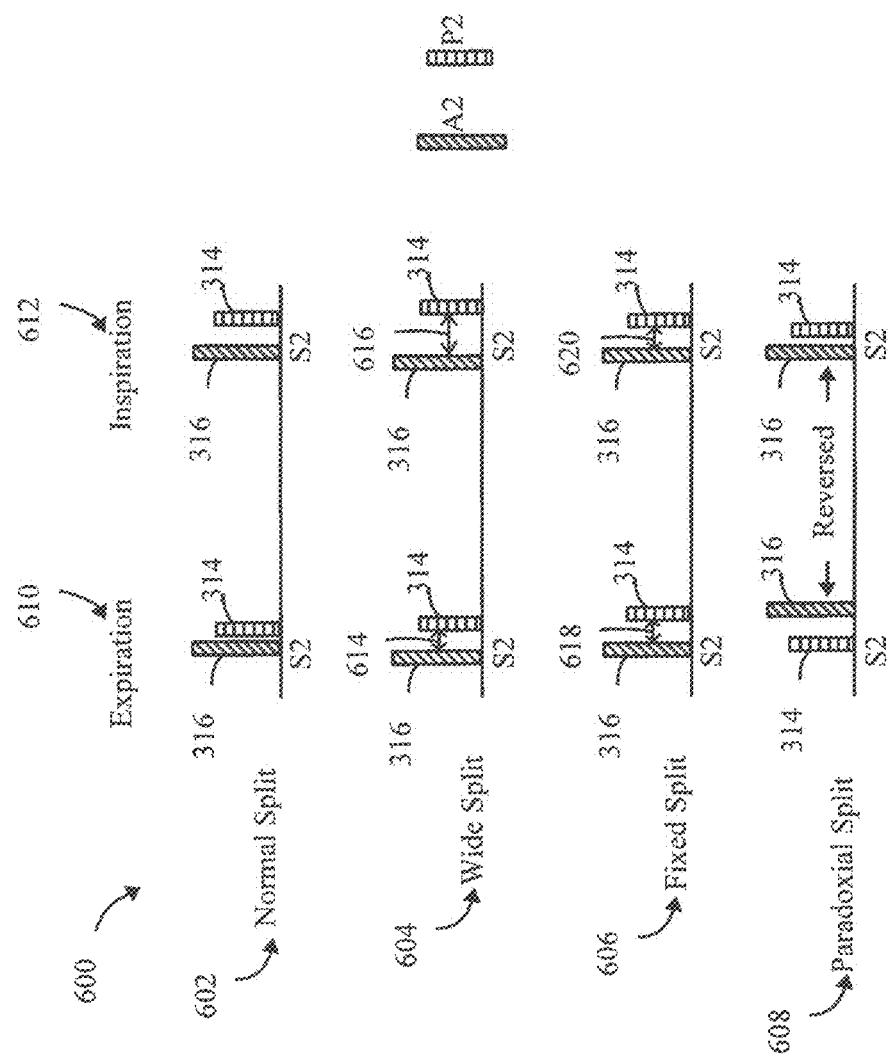
FIG. 6 illustrates a graphical representation of different types of S2 splits, in accordance with an embodiment.

FIG. 6 illustrates a graphical representation 600 of different types of S2 splits that may be exhibited, including a normal split 602, a wide split 604, a fixed split 606, and a paradoxical split 608. The A2 signal 314 and the P2 signal 316 are shown divided into the expiration phase 610 and the inspiration phase 612. The different types of split for the normal split 602, wide split 604, a fixed split 606, and the paradoxical split 608 may be determined in connection with one or more cardiac cycles and respiratory cycles for which heart sound signals and respiration signals are collected over a period of time by the IMD 100 and/or the microcontroller 164. For example, the period of time may represent years, months, days, and/or the like over a period of time.

The normal split 602 corresponds to a relation in which the A2 signal 314 and the P2 signal 316 are separated by a first/expiration time interval during the expiration phase and a second/inspiration longer time interval during the inspiration phase, where the first and/or second time intervals are less than corresponding predetermined normal split limits. For example, a normal split limit may be defined (e.g., manually programmed and/or automatically calculated). In order to be classified as a normal split, one or both of the expiration and inspiration time intervals should fall below the normal split limit. In addition, to be classified as a normal split, the first/expiration time interval is equal to or longer than the second/inspiration time interval by up to a predetermined limit. The inspiration and expiration time intervals may generally be referred to as split time intervals. The expiration-inspiration difference, between the first/expiration and second/inspiration time intervals corresponding to the separation between the A2 and P2 signals, may vary within a predetermined limit. Additionally or alternatively, a limit for the difference, between the first/expiration and second/inspiration time intervals, may be programmed to have a maximum upper difference. Additionally or alternatively, limits for the difference may be defined based on previous data collected in connection with the present patient and/or based on data collected in connection with a larger patient population.

The wide split 604 corresponds to a relation in which the A2 signal 314 and the P2 signal 316 are separated by a first/expiration time interval 614 during the expiration phase and a second/inspiration longer time interval 616 during the inspiration phase where the expiration and/or inspiration intervals 614, 616 are greater than corresponding predetermined limits. When one or both of the expiration and inspiration time intervals 614, 616 exceed the normal split limit, the combination is classified as a wide split 604. Additionally or alternatively, the combination may be classified as a wide split 604 when the inspiration time interval 616 exceeds the expiration time interval 614 by more than a predetermined expiration-inspiration difference. In accordance with embodiments herein, when a wide split 604 is identified, the IMD 100 may vary the RV and/or the LV delays to correct for the wide split 604. For example, the adjustment in the pacing delays of the RV and/or the LV may adjust the wide split 604, which may change the splits 614, 616 (e.g., the expiration and/or inspiration intervals 614, 616) to be within the normal split 602 range.

The fixed split 606 corresponds to a relation in which the A2 signal 314 and the P2 signal 316 are separated by a first/expiration time interval 618 during the expiration phase and a second/inspiration time interval 620 during the inspiration phase, where the expiration and inspiration time intervals 618, 620 are substantially similar or with when a relatively close interval of one another. For example, the microcontroller 164 may determine the splits 618, 620 (e.g., the expiration and inspiration time intervals 618, 620) may be similar to and/or the same relative to each other.

The paradoxical split 608 corresponds to a change in order of the A2 signal 314 and the P2 signal 316 relative to the order in the normal split 602. For example, during the expiration phase 610, the P2 signal 316 occurs prior to and/or before the A2 signal 314. Additionally or alternatively, the A2 signal 314 occurs prior to and/or before the P2 signal 316 during the inspiration phase 612. Based on the change of order of the A2 signal 314 and the P2 signal 316 between the expiration and/or inspiration phase is 610, 612, the microcontroller 164 may determine that paradoxical split 608 is present.

Cardiac Condition Matrix

FIG. 7 illustrates a cardiac condition matrix 700 formed in accordance with embodiments herein. The cardiac condition matrix 700 may be organized in various manners, such as in columns 702-708 related to different local heart regions, such as a right heart region, a left heart region, and a greater vessel region. The column 702 represents activation of the RV only pacing of the right ventricle. The column 704 represents activation of the LV only pacing of the left ventricle. The columns 706, 708 do not correspond to activation of the RV and/or LV pacing. Instead, column 706 corresponds to conditions related to the greater vessels, while column 708 corresponds to conditions related to the septum. The conditions recorded in the matrix 700 may be determined based on history and/or recording of the cardiac condition over time of the subject. The history and/or recording of the cardiac condition of the subject may be based on a period of years, days, months and/or the like of the subject stored in the memory 152.

The cardiac condition matrix 700 is also organized in rows 710-720 that correspond to different types of S2 splits. The cardiac condition matrix 700 further includes different cardiac conditions (CC) associated with each combination of the S2 split type and/or local heart region. By way of example, CC cell 722 in the matrix 700 indicates that, when an IMD provides RV only pacing and an S2 split type is identified to correspond to a wide split, the microcontroller 164 will identify a cardiac condition to represent right bundle branch block (RBBB) of the subject. As another example, CC cell 724 in the matrix 700 indicates that, when an IMD provides LV only pacing and an S2 split type is identified to correspond to a wide split, the microcontroller 164 will identify a cardiac condition to represent pre-excitation of left ventricle, left ventricle pacing, and/or premature LV beats.

As indicated at CC cell 726, when no pacing is provided, and a wide split is identified, the microcontroller 164 will identify the cardiac condition to represent pulmonic stenosis, pulmonary arterial hypertension. For example, one or more of the pulmonic stenosis and/or pulmonary arterial hypertension may be identified based on a history and/or recording the cardiac condition over time for the subject stored in the memory 152. The microcontroller 164 may determine the pulmonic stenosis and/or pulmonary arterial hypertension based on the history and/or recording the cardiac condition over time of the subject stored in the memory 152.

The matrix 700 further indicates that, when the S2 split type exhibits excessive split during expiration 714 and normal split during inspiration, during RV only pacing, the heart condition could be associated with the RV pacing. Alternatively, during LV only pacing, the heart condition corresponds to one or more of hypertrophic cardiomyopathy and/or left bundle branch block (LBBB). Alternatively, when no LV pacing and no RV pacing is applied, when excessive split occurs only during expiration, the cardiac condition is that the greater vessels are experiencing an aortic stenosis. For example, the aortic stenosis may be based on historical context and/or recording the cardiac condition over time for the subject stored in the memory 152.

The matrix 700 further indicates certain cardiac conditions that may be present when the S2 split type exhibits a fixed split during both inspiration and expiration 716. When the S2 split type is declared to exhibit a fixed split, when RV only pacing is present, the cardiac condition may indicate right heart failure. When the S2 split type is declared to exhibit a fixed split during LV only pacing, the cardiac condition may be unknown or indeterminate. When the S2 split type is declared to exhibit a fixed split during no LV pacing and no RV pacing, cardiac condition may indicate pulmonary hypertension.

The matrix 700 further indicates certain cardiac conditions that may be present when the S2 split type exhibits split during both inspiration and expiration 718, but not a fixed split. In connection with the condition at 718, when RV only pacing is applied, the cardiac condition may be unknown or indeterminate. When LV only pacing is applied, the cardiac condition may indicate LBBB, preexcitation of the RV, RV pacing related condition and/or premature RV beats.

The matrix 700 further indicates certain cardiac conditions that may be present when there is a loss of either the A2 signal or the P2 signal 720. The loss of A2 and/or P2 signals may occur in obese patients, patients with emphysema, or excess pericardial fluid. For example, the A2 and/or the P2 signals 314, 316 may be missing and/or lost by the heart sound sensor 170, the respiratory sensor 172, and/or the arrhythmia circuit 166. When the foregoing conditions are present, the P2 signal may not be properly sensed. When the condition at 720 is identified, the cardiac condition may be determined to represent severe aortic stenosis, severe aortic regurgitation, and/or congenital absence of pulmonary valve.

Optionally, a cardiac condition may transition between different types of S2 split. For example, a wide split 712 may occur after and/or subsequent to a normal split 710 of the subject. For example, the IMD 100 may determine that the subject has had the normal split 710 for a period of time stored in the memory 152. Responsive to the wide split 712, the microcontroller 164 may determine and/or identify the cardiac condition based on a comparison of the time interval of the S2 split in the cardiac condition matrix 700.

Figure 8:
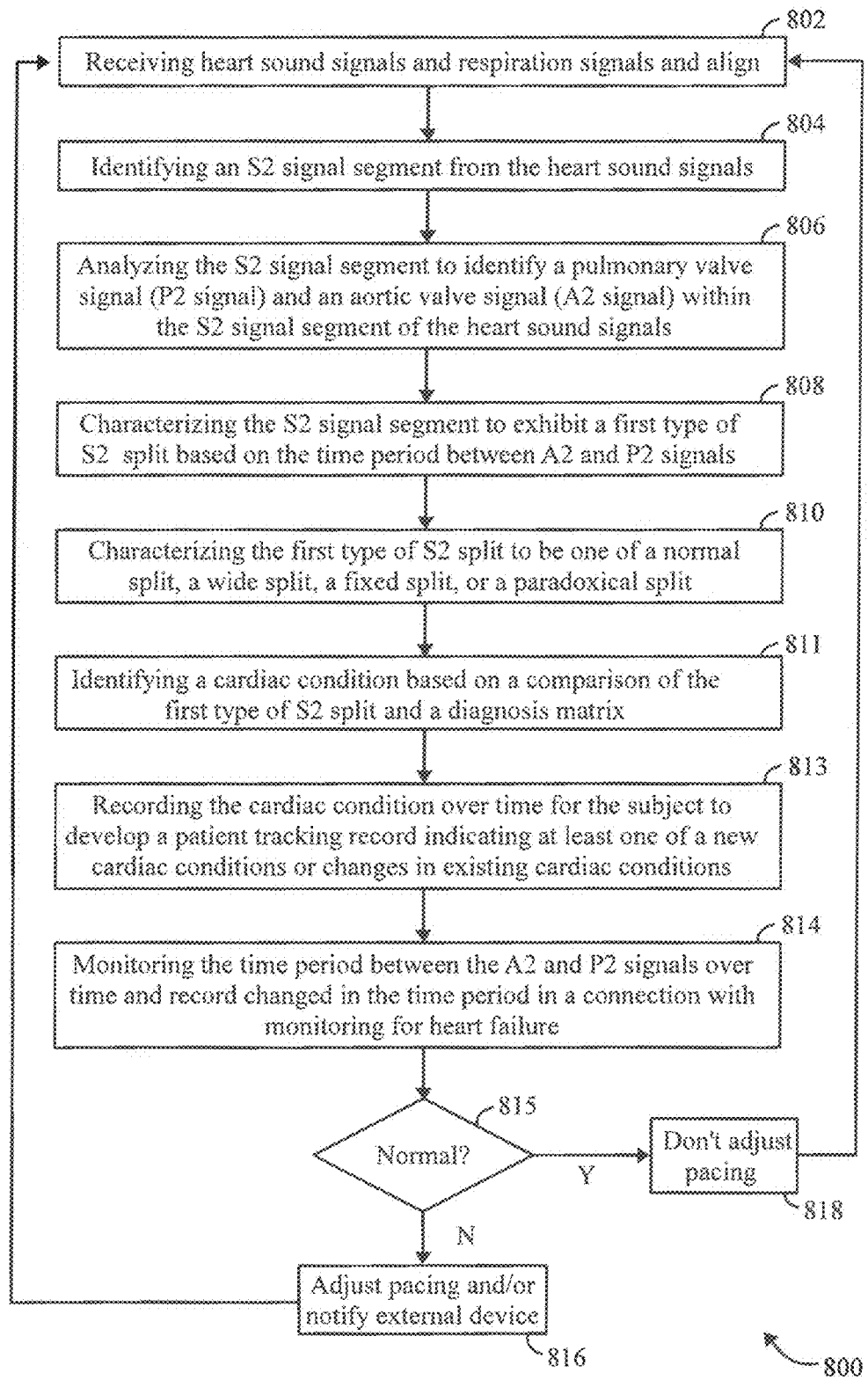
FIG. 8 illustrates a flowchart of a method implemented to identify cardiac conditions, in accordance with an embodiment.

FIG. 8 illustrates a method implemented in accordance with embodiments for herein for utilizing A2 and P2 signals to identify cardiac conditions. The method 800, for example, may employ or be performed by structures or assets of various embodiments (e.g., systems and/or methods and/or process flows) discussed herein. In various embodiments, certain steps may be omitted or added, certain steps may be combined, you certain steps may be performed concurrently, certain steps may be split into multiple steps, or certain steps may be performed in a different order.

Beginning at 802, the microcontroller 164 receives the heart sound signals 306. The heart sound sensor 170 measures an analog signal indicative of the heart sound signals 306. Optionally at 802, the microcontroller 164 receives respiration signals from the respiratory sensor 172. For example, the respiratory sensor 172 measures an analog signal indicative of the respiratory sound. For example, an amplitude, a frequency, and/or the like of the analog signal may increase relative to the increase in pressure of the lungs, representing an inspiration phase. Additionally or alternatively, the amplitude, the frequency, and/or the like of the analog signal may decrease relative to the loss in pressure of the lungs, representing an expiration phase. Based on the inspiration and expiration phases, the respiratory sensor 172 determines the respiratory phase of the subject. At 802, the microcontroller 164 aligns the heart sound signals and the respiration signals. Additionally or alternatively, the microcontroller 164 receives cardiac signal 308 from the arrhythmia circuit 166. For example, the arrhythmia circuit 166 is configured to monitor cardiac activity signals of the subject. Optionally, the arrhythmia circuit 166 may be utilized as an electromyography (EMG) sensor configured to detect a cardiac signal of the subject.

At 804, the microcontroller 164 identifies an S2 signal segment from the heart sound signals. Optionally, the microcontroller 164 may identify a respiratory phase from the respiratory signals, analyze the cardiac signals 308 and the like.

At 806, the microcontroller 164 analyzes the S2 signal segment to identify an A2 signal and a P2 signal within the S2 signal segment of the heart sound signals. For example, the microcontroller 164 may apply a bandpass filter 168 to the heart sound signals 306. For example, the bandpass filter 168 is configured to allow frequencies between 5-200 Hz of the heart sound signals 306 acquired by the heart sound sensor 170 to form the revised heart sound signals 316. Additionally or alternatively, the bandpass filter 168 is configured to allow frequencies between 0.05-1 Hz for the cardiac signal 308 and/or the respiratory signals 506A-C acquired by the respiratory sensor 172.

Optionally, the microcontroller 164 may align the revised heart sound signals 316 and the respiratory signals with each other. For example, the microcontroller 164 may align the revised heart sound signals 316 and the respiratory signals with the respiratory phases (e.g., the inspiration phase, the expiration phase). The microcontroller 164 may identify the A2 and P2 signals 314, 316 in connection with respiratory phases of interest based on the respiratory signals. The microcontroller 164 may identify combinations of the A2 signal 512 and the P2 signal 514 in conjunction with the expiration phase and inspiration phase. The microcontroller 164 identifies and saves combinations of inspiration and expiration time intervals. The inspiration time interval is between the A2 and P2 signals of the inspiration phase and the expiration time interval is between the A2 and P2 signals of the expiration phase.

At 808, the microcontroller 164 analyzes the inspiration and expiration time intervals and characterizes one or more S2 signal segments to exhibit a first type of S2 split based on the time intervals between the A2 and P2 signals during the corresponding phases of the respiratory cycle. Optionally, the microcontroller 164 compares the inspiration and expiration time intervals to a template. Additionally or alternatively, the microcontroller 164 may compare a difference between the inspiration and expiration time intervals with one or more templates stored in the memory 152. The templates may represent one or more different time intervals.

At 810, the microcontroller 164 characterizing the first type of S2 split to be one of a normal split 602, a wide split 604, a fixed split 606, or a paradoxical split 608. FIG. 6 illustrates examples of different types of splits and criteria to distinguish each type of split. At 811, the microcontroller 164 identifies the cardiac condition based on a comparison of the first type of the S2 split and the cardiac condition matrix 700. FIG. 7 illustrates examples of cardiac conditions that may be identified from the matrix 700.

At 813, the microcontroller 164 records the cardiac condition over time for the subject to develop a patient tracking record indicating at least one of a new cardiac conditions or changes in existing cardiac conditions. For example, the microcontroller 164 records the cardiac conditions received from the cardiac signal 308. The microcontroller 164 may identify the patient tracking record indicating at least one of the new cardiac conditions. For example, the microcontroller 164 may identify adjustments to the QRS complex 318, 319, and/or the like that may indicate changes in the heart 111 of the subject. Optionally, the microcontroller 164 may identify changes in the A2 signal 314 and/or the P2 signal 316 that may indicate a change in the normal split 602, the wide split 604, the fixed split 606, and/or the paradoxical split 608.

At 814, the microcontroller 164 monitors the split time intervals between the A2 and P2 signals over a period of time. The microcontroller 164 records changes in the split time intervals (e.g., inspiration and/or expiration time intervals) in connection with monitoring for heart failure. For example, the microcontroller 164 may identify changes in the split time interval that may represent adjustments from normal split 602 to at least one of the wide split 604, fixed split 606, and/or paradoxical split 608.

At 815, the microcontroller 164 determines whether the split time intervals are normal. For example, the microcontroller 164 may compare changes in the split time intervals relative to split time intervals associated with a normal split. When split time intervals are identified to change from a normal split to an abnormal split type, flow moves to 816. When the split time intervals remain normal, flow moves to 818. At 818, responsive to the determination by the microcontroller 164 that the heart sound includes a normal split 710, the microcontroller 164 may not adjust the pacing delays of the LV and/or the RV. The microcontroller 164 may not adjust the pacing delays of the RV and/or the LV pacing. Optionally, the microcontroller 164 may return to the operation 802 to receive heart sound signals of the subject.

At 816, the microcontroller 164 identifies adjustments to be automatically applied in connection with identifying at least one of the wide split 604, fixed split 606, and/or paradoxical split 608. For example, at 816, responsive to the determination of a cardiac condition (e.g., wide split 712, split duration expiration 714, split during both inspiration and expiration (e.g., fix split) 716, split during both inspiration and expiration 718, loss of A2 signal 314 and/or loss of P2 signal 316, the microcontroller 164 adjusts the pacing delays of the RV and/or the LV pacings, notify great vessels and/or septum. For example, the microcontroller 164 may adjust the pacing delays of the RV and/or the LV pacings to adjust the time interval between the A2 and the P2 signals 314, 316. The adjustment of the pacing delays may adjust the time interval, which may affect the wide split 604, the fixed split 606, and/or the paradoxical split 608. Additionally or alternatively, the microcontroller 164 may notify the external device 104 of the cardiac conditions of the great vessels and/or septum.

The foregoing operations at 816, 818 are described in connection with pacing features. Additionally or alternatively, adjustments may be made in connection with cardiac resynchronization therapy (CRT) timing delays. For example, based on the S2 split characterized and monitored, as described herein, a VV delay and/or an AV delay for a CRT device may be adjusted until the timing split approaches a normal split. In this alternative embodiment, at 816, the VV delay and/or AV delay of a CRT device would be adjusted and the operations of FIG. 8 repeated until the timing split was deemed normal at 815.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD), comprising:
   one or more sensors configured to be implanted in a subject and to sense heart sound signals of the subject;
   a respiration sensor configured to sense respiration signals of the subject;
   a memory configured to store program instructions; and
   a processor that, when executing the program instructions, is configured to:
      identify S2 signal segments from the heart sound signals;
      analyze the S2 signal segments to identify corresponding pulmonary valve signals (P2 signals) and aortic valve signals (A2 signals);
      identify expiration and inspiration phases from the respiration signals;
      determine an expiration time interval between the corresponding A2 and P2 signals during the expiration phase;
      determine an inspiration time interval between the corresponding A2 and P2 signals during the inspiration phase;
      characterize the S2 signal segments to exhibit a first type of S2 split based on a relation between the expiration and inspiration time intervals; and
      identify a cardiac condition based on the first type of the S2 split, where the cardiac condition is utilized to determine at least one of a therapy or change in therapy for the subject.

2. The IMD of claim 1, wherein the processor is configured to characterize the first type of S2 split to be one of a normal split, a wide split, a fixed split, or a paradoxical split based on a comparison of a) the expiration time interval between the corresponding A2 and P2 signals during the expiration phase and b) the inspiration time interval between the A2 and P2 signals during the inspiration phase.

3. The IMD of claim 1, wherein the processor is configured to identify the cardiac condition based on a cardiac condition matrix that is divided based on multiple types of the S2 split and multiple local heart regions, the cardiac condition matrix further including different cardiac conditions associated with each combination of the S2 split type and local heart region, the cardiac condition matrix stored in the memory.

4. The IMD of claim 3, wherein the local heart regions include a right heart region, a left heart region, and a greater vessel region, the processor configured to identify the first type of the S2 split to correspond to at least one of a right heart-related condition, left heart-related condition, or greater vessel-related condition.

5. The IMD of claim 1, wherein the processor is configured to apply a bandpass filter to the respiration signal to identify the P2 signal and the A2 signal from the S2 signal segment.

6. The IMD of claim 5, wherein the respiration sensor comprises at least one of an accelerometer, a pressure sensor, or an impedance sensor that is configured to indicate a respiratory phase of the subject.

7. The IMD of claim 1, wherein the processor is configured to extract the P2 signal and the A2 signal based on a peak of the A2 signal and a slope of the P2 signal.

8. The IMD of claim 1, wherein the processor is configured to record the cardiac condition over time for the subject.

9. The IMD of claim 8, wherein the processor is configured to develop a patient tracking record indicating at least one of new cardiac conditions or changes in existing cardiac conditions.

10. The IMD of claim 1, wherein the processor is configured to monitor the expiration and inspiration time intervals over time and record changes in the expiration and inspiration time intervals in connection with monitoring for heart failure.

11. The IMD of claim 1, further comprising a pulse generator to deliver pacing therapy based in part on programmed delays, wherein the processor is configured to monitor the time signals between the A2 and P2 signals over time and record changes in the time signals in connection with adjustments in at least one of the programmed delays.

12. The system of claim 1, wherein the processor is configured to repeat the identify, analyze and determine operations in connection with the inspiration and expiration phases of the one or more respiration cycles.

13. A computer implemented method, comprising:
sensing, at one or more sensors of an implantable medical device (IMD), heart sound signals of a subject, the one or more sensors configured to be implanted in the subject;
sensing, at a respiration sensor of the IMD, respiration signals of the subject;
utilizing a processor of the IMD for,
identifying S2 signal segments from the heart sound signals;
analyzing the S2 signal segments to identify corresponding pulmonary valve signals (P2 signals) and aortic valve signals (A2 signals) within the S2 signal segments of the heart sound signals;
identifying expiration and inspiration phases from respiration signals;
determining an expiration time interval between the corresponding A2 and P2 signals during the expiration phase;
determining an inspiration time interval between the corresponding A2 and P2 signals during the inspiration phase;
characterizing the S2 signal segments to exhibit a first type of S2 split based on a relation between the expiration and inspiration time intervals; and
identifying a cardiac condition based on the first y type of S2 split, where the cardiac condition is utilized to determine at least one of a therapy or change in therapy for the subject.

14. The method of claim 13, further comprising characterizing the first type of S2 split to be one of a normal split, a wide split, a fixed split, or a paradoxical split based on a comparison of a) the expiration time interval between the corresponding A2 and P2 signals during the expiration phase and b) the inspiration time interval between the A2 and P2 signals during the inspiration phase.

15. The method of claim 14, wherein the local heart regions include a right heart region, a left heart region, and a greater vessel region; and
further comprising identifying the first type of the S2 split to correspond to at least one of a right heart-related condition, a left heart-related condition, or a greater vessel-related condition.

16. The method of claim 13, further comprising extracting the P2 signal and the A2 signal based on a peak of the A2 signal and a slope of the P2 signal relative to the respiratory phase.

17. The method of claim 13, further comprising recording the cardiac condition over time for the subject to develop a patient tracking record indicating at least one of a new cardiac conditions or changes in existing cardiac conditions.

18. The method of claim 13, wherein the identifying, analyzing and determining operations are repeated in connection with the inspiration and expiration phases of the one or more respiration cycles.

* * * * *